United States Patent [19]

Agaskar et al.

[11] Patent Number: 5,530,171

[45] Date of Patent: Jun. 25, 1996

[54] PROCESS FOR THE CATALYTIC DEHYDROGENATION OF ALKANES TO ALKENES WITH SIMULTANEOUS COMBUSTION OF HYDROGEN

[75] Inventors: Pradyot A. Agaskar, Lawrenceville, N.J.; Robert K. Grasselli, Chadds Ford, Pa.; James N. Michaels, Neshanic Station, N.J.; P. Thomas Reischman, Lambertville, N.J.; David L. Stern, Lawrenceville, N.J.; John G. Tsikoyiannis, Princeton, N.J.

[73] Assignee: Mobil Oil Corporation, Fairfax, Va.

[21] Appl. No.: 423,629

[22] Filed: Apr. 17, 1995

Related U.S. Application Data

[63] Continuation-in-part of Ser. No. 112,289, Aug. 27, 1993, abandoned.

[51] Int. Cl.$^6$ .................................................. C07C 5/333
[52] U.S. Cl. ........................... 585/659; 585/654; 585/656; 585/658
[58] Field of Search ..................................... 585/621, 626, 585/630, 631, 629, 658, 656, 659, 660, 662, 663

[56] References Cited

U.S. PATENT DOCUMENTS

| | | | |
|---|---|---|---|
| 2,985,596 | 5/1961 | Pitzer | 585/654 |
| 3,501,547 | 3/1970 | Nolan et al. | 260/680 |
| 3,937,748 | 2/1976 | Miklas | 260/680 E |
| 4,327,238 | 4/1982 | Eastman | 585/661 |
| 4,368,346 | 1/1983 | Eastman | 585/658 |
| 4,435,607 | 3/1984 | Imai | 585/443 |
| 4,476,344 | 10/1984 | Kimble | 585/661 |
| 4,652,687 | 3/1987 | Imai et al. | 585/319 |
| 4,727,216 | 2/1988 | Miller | 585/660 |
| 4,739,124 | 4/1988 | Ward | 585/658 |
| 4,788,371 | 11/1988 | Imai et al. | 585/443 |
| 4,806,624 | 2/1989 | Herber et al. | 585/440 |
| 4,827,066 | 5/1989 | Herber et al. | 585/319 |
| 4,921,828 | 5/1990 | Brazdil et al. | 502/205 |
| 4,940,826 | 7/1990 | Freide et al. | 585/600 |
| 4,990,714 | 2/1991 | Nemet-Mavrodin | 585/407 |
| 5,071,814 | 12/1991 | Sasaki et al. | 502/205 |
| 5,086,032 | 2/1992 | Mazzocchia et al. | 502/315 |

FOREIGN PATENT DOCUMENTS

568303A2  11/1993  European Pat. Off. .

OTHER PUBLICATIONS

Ziaka, Z. D. et al., "A High Temperature Catalytic Membrance Reactor for Propane Dehydrogenation," J. of Membrane Science, 77, 221–232 (1993).

Shu, J. et al., Canadian Journal of Chemical Engineering, vol. 69, 1036–1060 (1991).

*Primary Examiner*—Asok Pal
*Attorney, Agent, or Firm*—Ronald A. Bleeker; Malcolm D. Keen; Peter W. Roberts

[57] ABSTRACT

There is provided a process for the net catalytic oxidative dehydrogenation of alkanes to produce alkenes. The process involves simultaneous equilibrium dehydrogenation of alkanes to alkenes and combustion of the hydrogen formed to drive the equilibrium dehydrogenation reaction further to the product alkenes. In the present reaction, the alkane feed is passed into a reactor containing both an equilibrium dehydrogenation catalyst and a reducible metal oxide, whereby the alkane is dehydrogenated and the hydrogen produced is simultaneously and selectively combusted in oxidation/ reduction (REDOX) reaction with the reducible metal oxide. This particular mode of operation is termed a same reactor, REDOX mode. The equilibrium dehydrogenation catalyst may comprise platinum and the reducible metal oxide may contain bismuth, antimony, indium, or molybdenum, or a mixture thereof.

17 Claims, 2 Drawing Sheets

PROCESS FOR THE CATALYTIC DEHYDROGENATION OF ALKANES TO ALKENES WITH SIMULTANEOUS COMBUSTION OF HYDROGEN

CROSS-REFERENCE TO RELATED APPLICATION

This application is a continuation-in-part of copending U.S. application Ser. No. 08/112,289, filed Aug. 27, 1993 now abandoned.

BACKGROUND

There is provided a process for the net catalytic oxidative dehydrogenation of alkanes to produce alkenes. The process involves simultaneous equilibrium dehydrogenation of alkanes to alkenes and combustion of the hydrogen formed to drive the equilibrium dehydrogenation reaction further to the product alkenes.

Developments in zeolite catalysts and hydrocarbon conversion processes have created interest in utilizing light aliphatic feedstocks for producing $C_5+$ gasoline, diesel fuel, etc. In addition to chemical reactions promoted by medium-pore zeolite catalysts, a number of discoveries have contributed to the development of new industrial processes. These are safe, environmentally acceptable processes for utilizing aliphatic feedstocks. Conversions of $C_2$–$C_4$ alkenes and alkanes to produce aromatics-rich liquid hydrocarbon products were found by Cattanach (U.S. Pat. No. 3,760,024) and Yan et al. (U.S. Pat. No. 3,845,150) to be effective processes using the zeolite catalysts. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062; 4,211,640; and 4,227,992. The above-identified disclosures are incorporated herein by reference.

Catalytic dehydrogenation and aromatization of light paraffinic streams, e.g., $C_2$–$C_4$ paraffins, commonly referred to as LPG, is strongly endothermic and typically carried out at temperatures between 540° and 820° C. (1000° and 1500° F.), the problem of transferring sufficient heat to a catalytic reaction zone to carry out the paraffin upgrading reaction remains as an obstacle to commercialization of these processes.

Dehydrogenation of paraffins to olefins has recently generated increasing interest as the market value of olefinic intermediate feedstocks continues to rise. Light olefins, particularly $C_2$–$C_4$ olefins, enjoy strong demand as building blocks for a wide range of valuable end products including fuels and specialized lubricants as well as thermoplastics.

Methods for supplying heat to an endothermic reaction zone include indirect heat exchange as well as direct heat exchange. Indirect heat exchange is exemplified by a multi-bed reactor with inter-bed heating or a fluid bed reactor with heat exchange coils positioned within the catalyst bed. Direct heat exchange techniques include circulation of inert or catalytically active particles from a high temperature heat source to the reaction zone, or the coupling of a secondary exothermic reaction with the primary endothermic reaction in a single catalytic reaction zone. Examples of such secondary exothermic reactions include (1) oxidative dehydrogenation of a portion of the feedstream, (2) sacrificial co-combustion of a part of the alkane/alkene mixture, and (3) combustion of carbonized species (e.g., coke) on the catalyst.

Currently known techniques for oxidative dehydrogenation are unfortunately not selective enough to achieve sufficiently high levels to allow for commercial practice and at least a part of the valuable product is over-oxidized, usually to the waste products, CO, $CO_2$, and $H_2O$.

Examples of such sacrificial co-combustion processes include those described in U.S. Pat. No. 3,136,713 to Miale et al. which teaches a method for heating a reaction zone by selectively burning a portion of a combustible feedstream in a reaction zone. Heat is directly transferred from the exothermic oxidation reaction to supply the endothermic heat for the desired conversion reaction.

A process for the oxidative dehydrogenation of propane is described in U.S. Pat. No. 5,086,032 to Mazzocchia et al.

Heat balanced reactions are also taught in U.S. Pat. Nos. 3,254,023 and 3,267,023 to Miale et al. Additionally, U.S. Pat. No. 3,845,150 to Yan and Zahner teaches a heat balanced process for the aromatization of hydrocarbon streams by combining the exothermic aromatization of light olefins with the endothermic aromatization of saturated hydrocarbons in the presence of a medium-pore zeolite catalyst.

Turning now to chemical reaction thermodynamics, it is well recognized that the extent of reaction may be increased by removing reaction products from contact with the reactants as the reaction products are formed. This principle finds application in U.S. Pat. No. 3,450,500 to Setzer et al. which teaches a process for reforming hydrocarbon feedstocks and withdrawing the hydrogen product from contact with the feedstock driving the equilibrium to favor increased hydrogen production. Articles by Shu et al. and by Ziaka et al. teach that the extent of reaction for equilibrium dehydrogenation reactions may be further driven to product olefin by the concomitant removal of the hydrogen formed with hydrogen selective membranes. The article by Shu et al. appears in the *Canadian Journal of Chemical Engineering*, 69, 1036–1060 (1991); and the article by Ziaka et al. entitled "A High Temperature Catalytic Membrane Reactor for Propane Dehydrogenation" appears in the *Journal of Membrane Science*, 77, 221–232 (1993).

Similarly, British Patent Application GB 2190397A describes a process for producing aromatic hydrocarbons by catalytic paraffin dehydrocyclodimerization. The process upgrades $C_2$–$C_6$ paraffins, i.e., ethane, propane, butane or a mixture thereof to a mixture of aromatic hydrocarbons and hydrogen by-product in a reactor provided with a membrane capable of selective, in-situ transfer of at least a portion of the hydrogen in the mixture across the membrane. Catalysts useful in the paraffin upgrading process are said to include zeolites, and in particular gallium-containing zeolites.

It is believed that the paraffin dehydrogenation reaction is equilibrium limited when carried out in a conventional reactor due to the thermodynamics of equilibrium dehydrogenation. For example, at 550° C. the equilibrium propylene from propane dehydrogenation, irrespective of catalyst, is limited to 33%. Thus, the state of the art of endothermic hydrogen-producing paraffin upgrading processes would clearly be advanced by a process and apparatus for increasing the extent of reaction while also providing a high temperature heat source to supply at least a portion of the endothermic heat of reaction.

SUMMARY

There is provided a process for converting an alkane of the formula, $C_nH_{2n+2}$, to an alkene of the formula, $C_nH_{2n}$, where n is the same for said alkane and said alkene and n is from 2 to 5, said process comprising contacting said alkane in the absence of cofed oxygen with a dehydrogenation catalyst and a solid oxygen source comprising a reducible metal oxide under conditions sufficient to selectively convert said alkane and reducible metal oxide to a reduced form of the metal oxide, said alkene, and water, wherein said dehydrogenation catalyst comprises at least one metal selected from the group consisting of Cr, Mo, Ga, Zn, and a Group VIII metal, and wherein said reducible metal oxide is an oxide of at least one metal selected from the group consisting of Bi, In, Sb, Zn, Tl, Pb and Te.

EMBODIMENTS

Figure 1:
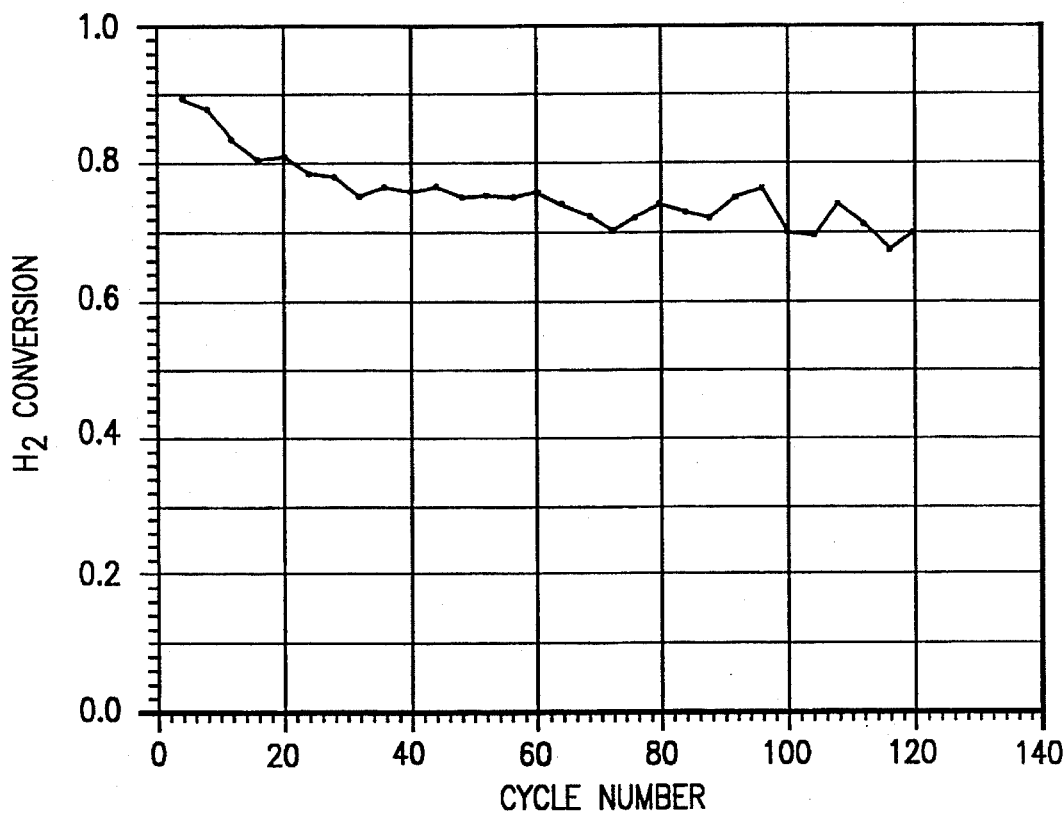
FIG. 1 is a graph showing conversion of $H_2$ and propylene over $Bi_2O_3/SiO_2$ during the course of 120 REDOX cycles.

Alkanes are converted to olefins (and dienes) by an integrated process scheme which involves the direct equilibrium dehydrogenation of alkanes via known catalysts and the selective oxidation of the resulting hydrogen gas thus formed. The light paraffins which may be utilized for such reactions include $C_2$–$C_5$, such as propane and isobutane. As an illustrative example, the overall reaction scheme, demonstrated for propane oxidative dehydrogenation, is thus:

Scheme A:

$$C_3H_8 \xrightarrow{Cat. 1} C_3H_6 + H_2 \quad \quad 1.$$

$$H_2 + M_x{}^nO_y \longrightarrow H_2O + M_x{}^{n-2}O_{y-1} \quad \quad 2.$$

$$C_3H_8 + M_x{}^nO_y \longrightarrow C_3H_6 + H_2O + M_x{}^{n-2}O_{y-1} \quad \quad A.$$

Reaction 1 is documented in the literature and is known as propane equilibrium dehydrogenation. Butane and isobutane equilibrium dehydrogenation are also known and documented in the literature. Reaction 1 has been demonstrated to occur catalytically over $Cr/Al_2O_3$, $Mo/Al_2O_3$, iron-based catalysts, supported (supports include silica, alumina, zirconia, titania, and thoria) and unsupported noble metals (e.g., Pt, Pd, Rh, Ir, Ru, etc.), and supported and unsupported gallium and zinc oxides. Reaction 2 can proceed in the absence (redox mode), as opposed to the presence (cofed mode) of gaseous oxygen, over a number of reducible metal oxides. Catalyst 1 and $M_x{}^nO_y$ may be used together or in separate reactors.

Several recent, open literature reports have discussed the oxidative dehydrogenation of propane and butane to the corresponding olefins. These reactions are typically carried out by utilizing a mixture of alkane and oxygen cofed over a metal oxide catalyst. Typical operating temperatures are from 400° to 600° C., 1–5 atm. pressure, either with a diluent or in the absence of one.

The present invention differs from the system described above in that the reaction involves two separately functioning materials an equilibrium dehydrogenation catalyst, and a solid oxygen source for selective hydrogen combustion. These components may be used in separate reactors, connected in series or in a recycle mode, so as to drive the equilibration reaction (equation 1 above) further to the product side than is normally possible with only an equilibration catalyst. Thus, in the present scheme, the hydrogen would be combusted to $H_2O$ (or at least a portion of it), thus driving the equilibrium represented by equation 1 to the side of the products.

The catalyst used in the dehydrogenation reaction may be an equilibrium dehydrogenation catalyst comprising a Group VIII metal (i.e., Fe, Co, Ni, Ru, Rh, Pd, Os, Ir or Pt). Of these Group VIII metals, the noble metals (i.e., Ru, Rh, Pd, Os, Ir and Pt) are preferred. These Group VIII metals are preferably present in an at least partially reduced state with at least a portion thereof being in the free metal (i.e., zero valent) form. Examples of such equilibrium dehydrogenation catalysts include Pt, Pd, or other Group VIII metals either in bulk phase or supported on oxide supports (alumina, silica, titania, zirconia, zinc aluminate, etc.).

A particular dehydrogenation catalyst, which may be used in the present dehydrogenation reaction is a Pt/Sn/ZSM-5 catalyst, especially as described in U.S. Pat. Nos. 4,990,710 and 5,192,728. Such Pt/Sn/ZSM-5 catalysts may comprise 0.1 to 20 weight percent platinum and 0.1 to 20 weight percent tin with the remainder being ZSM-5. The ZSM-5 in this catalyst is essentially non-acidic and may comprise less than 0.1 weight percent of aluminum.

By means of the present invention, whereby hydrogen is selectively oxidized after being produced in the dehydrogenation of an alkane, it is possible to obtain greater than equilibrium yields of alkenes from the overall process. The following table provides thermodynamic calculations of equilibrium yields of propylene, butene, and isobutene from propane, n-butane, and i-butane, respectively.

| Temperature, °C. | Propane | n-Butane | i-Butane |
| --- | --- | --- | --- |
| 350 | 2 | 3 | 4 |
| 400 | 4 | 7 | 8 |
| 450 | 9 | 15 | 18 |
| 500 | 18 | 28 | 33 |
| 550 | 32 | 46 | 53 |
| 600 | 50 | 66 | 72 |
| 650 | 68 | 82 | 85 |
| 700 | 82 | 92 | 93 |

As described in the Examples below, particularly selective combustion of hydrogen over alkanes or alkenes is not a property common to all reducible metal oxides but rather is limited over a fairly narrow selection of metal oxides found to possess this particularly selective hydrogen combustion capability.

The reducible metal oxides, which are useful for promoting selective hydrogen combustion, must first have the property of being reducible under the present oxidation conditions so as to provide a source of oxygen to combust $H_2$. Accordingly, essentially nonreducible, essentially inert oxides, such as silica, would not fit this first criteria. A second criteria, which the present reducible oxide must fit, is that it provides oxygen in a selective manner, whereby it selectively causes $H_2$ to be converted to $H_2O$ without also oxidizing substantial quantities of the hydrocarbons (i.e., alkanes and alkenes) present. An example of such a nonselective reducible metal oxide, which tends to oxidize substantial quantities of hydrocarbons is vanadium oxide.

As is shown in Examples below, the oxides of bismuth are particularly selective for hydrogen combustion over hydrocarbon combustion, while the oxides of vanadium are not.

The reducible metal oxides, which are particularly selective for the present selective hydrogen combustion reaction, contain certain metals selected from a narrow quadrant of the periodic table, i.e., the upper right hand corner thereof. These metals include Bi, In, Sb, Zn, Tl, Pb and Te. A review of the periodic table suggests that this group of elements is centered by the location of the particular elements, Bi, In and Sb.

In addition to the reducible metal oxide, the solid oxygen source may include other components such as supports for the reducible metal oxide. Examples of such supports include nonreducible, essentially inert oxides, such as silica, alumina, zirconia, titania, hafnia, and mixtures of these oxides, such as silica/alumina. Other optional components of the present solid oxygen source include certain elements, particularly in oxide form, which have been used as promoters for known oxidation or oxidative dehydrogenation catalysts. Particular examples of oxides, which may be optionally included in the present solid oxygen source, include one or more oxides of elements selected from the group consisting of Mo, W, P and La. Although the question of whether such oxides of Mo, W, P and La actually have a beneficial or promoting effect in the present selective hydrogen combustion reaction has been largely unexplored, it is at least believed that these particular oxides do not have a detrimental effect.

Although oxides of Mo, W, P and La, as well as oxides of Si, Al, Zr, Ti and Hf, need not be avoided in the present solid oxygen source, other oxides, which tend to promote the oxidation of alkanes and alkenes, should be avoided. Examples of such oxides, which are preferably not included in the present solid oxygen sources, include oxides of one or more of the following elements: V, Fe, Cu, Nb and Ta.

The solid oxygen source may contain, for example, at least 1 wt. % of reducible metal oxide. Elemental analysis of the solid oxygen source may reveal the presence of, for example, at least 0.5 wt. % of one or a combination of metals selected from the group consisting of Bi, In, Sb, Zn, Tl, Pb and Te.

The solid oxygen source described herein may be an oxide of a single metal, such as bismuth or antimony, or it may be a mixed metal oxide. An example of a mixed metal oxide is a compound of the following empirical formula $$Bi_aSb_bTe_cA_dB_eC_fO_x$$

where
A = P, La, Ce, Y, Ru, Co, Ni, Al, In, Ga, and/or Ge
B = Mo, W, Cr, Sn, Nb, Ta, and/or Ti
C = an alkali, an alkaline earth, Ag, and/or Tl
O = oxygen
where a,b,c = 0 to 12
a+b+c > 0
d = 0 to 12
e = 0 to 12
f = 0 to 12
x = dictated by the oxidation states of the remaining elements.

Another example of a mixed metal oxide is a compound of the following empirical formula $$A_aB_bC_cD_dO_x$$

where
A = In, Cr, Al, Zn, Pb, and/or a Rare Earth (preferred RE = Tb, Gd, Ce, Y, and/or La)
B = La, Ce, Y, Ru, Fe, Co, Ni, Cu, Al, In, Ga, and/or Ge
C = P, Mo, W, Cr, Sn, Nb, Ta, and/or Ti
D = an alkali, an alkaline earth, Ag, and/or Tl
O = oxygen
where
0 < a < 12
b=0 to 12
c=0 to 12
d=0 to 12
e=0 to 12
x = dictated by the oxidation states of the remaining elements.

The combined dehydrogenation catalyst and solid oxygen source may be a homogeneous or heterogeneous material. An example of such a homogeneous material is formed when a Group VIII metal and a reducible metal oxide are coimpregnated, in a simultaneous or step-wise fashion, onto a common support material. However, the Group VIII metal and the reducible metal oxide may also be a heterogeneous material, wherein they are present as a mere physical mixture of separately formed materials, e.g., supported by different supports. Such heterogeneous materials, wherein discrete particles of dehydrogenation catalyst are physically mixed with discrete particles of solid oxygen sources, are contrasted with homogeneous oxidative dehydrogenation catalysts, wherein the active components thereof are coprecipitated into a homogeneous mass.

EXAMPLE 1

In this Example, it is demonstrated that some metal oxides can be reduced much faster by hydrogen than by hydrocarbons; hence, they exhibit superior selective hydrogen combustion (SHC) properties.

A gravimetric, Cahn balance apparatus was used to measure the reduction rates of several metal oxides with hydrogen and $C_3$ hydrocarbons at 500° C. These rates and the selectivity of the examined oxides for SHC are listed in Table 1.

In Table 1, MCC (multicomponent catalyst) stands for a compound of the formula $$Cs_{0.5}Ni_{2.5}Co_{4.5}Fe_3BiSbMo_{12}O_x,$$

where X is dictated by the oxidation states of the remaining elements. Also in Table 1, $[O]_L$ stands for lattice oxygen.

TABLE 1

Selectivities of SHC Catalysts at 500° C. for the Removal of Lattice Oxygen to Convert Hydrogen vs. Propane, Measured by Gravimetry

| Metal Oxide | Wt. % $[O]_L$ Removed in 5 min. by: | | Hydrogen to form water[a] | Propane to form propylene, $CO_x$, and water[b] |
|---|---|---|---|---|
| | Hydrogen | Propane | | |
| $Bi_2Mo_3O_{12}$ | 10.2 | 0.10 | 99.0 | 1.0 |
| $In_2Mo_3O_{12}$ | 12.9 | 0.21 | 98.4 | 1.6 |
| $Al_2Mo_3O_{12}$ | 5.36 | 0.25 | 95.5 | 4.5 |
| $Bi_2O_3$ | 8.85 | 0.44 | 95.3 | 4.7 |
| $Fe_2Mo_3O_{12}$ | 3.32 | 0.21 | 94.0 | 6.0 |
| MCC | 8.6 | 0.95 | 90.1 | 9.9 |
| $Cr_2Mo_3O_{12}$ | 6.97 | 0.91 | 88.5 | 11.5 |
| $La_2Mo_3O_{12}$ | 1.02 | 0.17 | 85.7 | 14.3 |
| $Ce_2Mo_3O_{12}$ | 1.04 | 0.27 | 79.4 | 20.6 |
| $MoO_3$ | 1.0 | 0.28 | 78.1 | 21.9 |
| $V_2O_5$ | 0.9 | 13.6 | 6.2 | 93.8 |

[a] % selectivity for $H_2$ =
$$\frac{\text{wt. \% } [O]_L \text{ removed by } H_2}{\text{wt. \% } [O]_L \text{ removed by } H_2 + \text{wt. \% } [O]_L \text{ removed by } C_3°}$$

[b] % selectivity for $C_3°$ =
$$\frac{\text{wt. \% } [O]_L \text{ removed by } C_3°}{\text{wt. \% } [O]_L \text{ removed by } C_3° + \text{wt. \% } [O]_L \text{ removed by } H_2}$$

Table 1 shows that $Bi_2O_3$, indium, bismuth, lanthanum, cerium, and aluminum molybdates; and MCC exhibit the highest selectivities for hydrogen combustion in the presence of propane, while $V_2O_5$ exhibits the lowest.

EXAMPLE 2

An equimolar mixture of 15% hydrogen and 15% propylene in helium was passed over 1 g of 42% $Bi_2O_3$/58% $SiO_2$ at a total flowrate of 170 cc/min at 550° C. for 140 seconds. The product gas was collected and analyzed with gas chromatography. $H_2$ conversion to $H_2O$ was greater than 85%, while the conversion of propylene was less than 0.5%.

EXAMPLE 3

The same experiment was conducted as in Example 2, except that the feed was flowed over the sample for 600 seconds at a total flowrate of 40 cc/min. The $H_2$ conversion in the reactor effluent was 79%, while the conversion of propylene was approximately 1%.

EXAMPLE 4

An equimolar mixture of 15% hydrogen and 15% propane in helium was passed over 1 g of 50% $V_2O_5$/50% $Al_2O_3$ at a total flowrate of 170 cc/min at 550° C. for 140 seconds. The product gas was collected and analyzed with gas chromatography. $H_2$ conversion to $H_2O$ was 81%, while the conversion of propane, mostly to CO, $CO_2$, and $H_2O$, was 23%.

EXAMPLE 5

The same experiment was conducted as in Example 4, except that the feed was flowed over the sample for 600 seconds at a total flowrate of 40 cc/min. The $H_2$ conversion in the reactor effluent was only 11%, while the conversion of propane to waste products was 24%. Examples 4 and 5 illustrate that, in sharp contrast to $Bi_2O_3$, $V_2O_5$ does not exhibit SHC properties, since its lattice oxygen is particularly active for the conversion of hydrocarbons.

EXAMPLE 6

The same material as in Examples 2 and 3 was exposed to 120 consecutive redox cycles. A redox cycle consists of an oxidation phase (flow of excess air for 5 minutes) followed by a reduction phase (flow of 15% $H_2$, 15% $C_3$ at 170 cc/min for 140 seconds). The oxidation and reduction phases are separated by two helium purge phases. The $H_2$ conversion as a function of cycle number is shown in FIG. 1. The conversion of propylene was negligibly small (less that 0.5%), mostly to $CO_2$. The conversion of $H_2$ is attributed to its oxidation to $H_2O$ by the lattice oxygen of $Bi_2O_3$ which did not oxidize virtually any of the hydrocarbon present.

EXAMPLE 7

In this Example, it is demonstrated that $Bi_2O_3$ is selective for combustion of $H_2$ in the presence of hydrocarbons and also in the presence of cofed gaseous oxygen.

Figure 2:
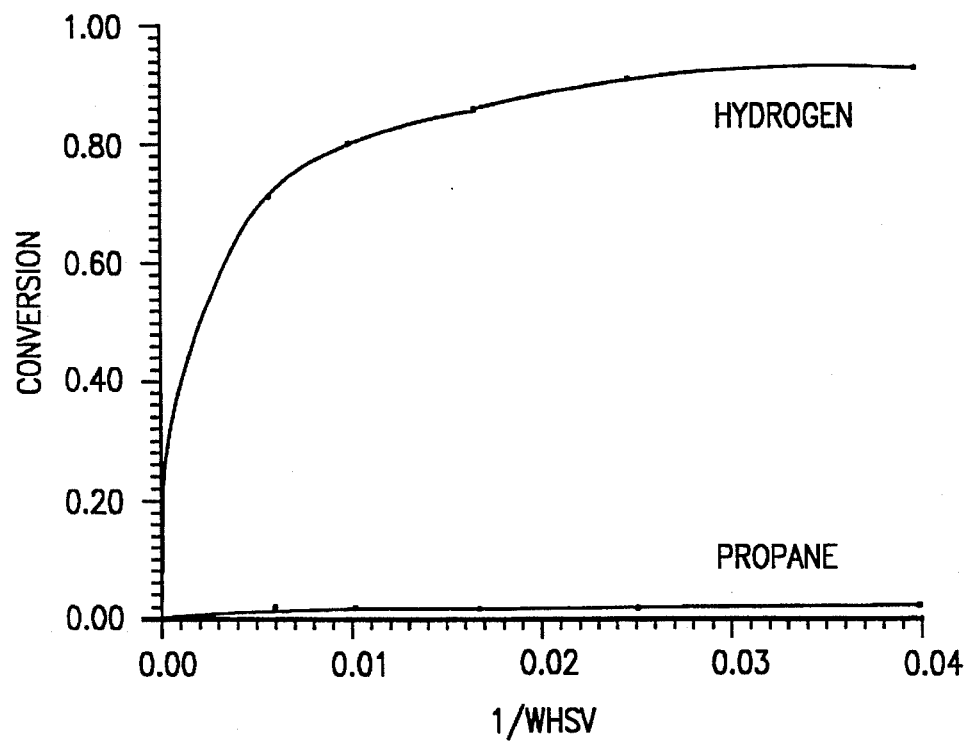
FIG. 2 is a graph showing conversions of hydrogen and propane as a function of residence time in a reactor.

The activity and selectivity of $Bi_2O_3$ in the cofed mode was examined using equimolar $H_2$-$C_3°$ and $H_2$-$C_3$ mixtures, with stoichiometric amounts of gaseous oxygen (15% $C_3°$, 15% $H_2$, 7.5% $O_2$). Shown in FIG. 2 are the conversions of hydrogen and propane at 500° C. as a function of residence time. The propane conversion, mostly to $CO_2$, was always less than 2%, while the conversion of hydrogen exceeded 90% at high residence time. This indicates that the deliberately limited supply of cofed oxygen had been utilized very selectively to preferentially activate the hydrogen gas.

Figure 3:
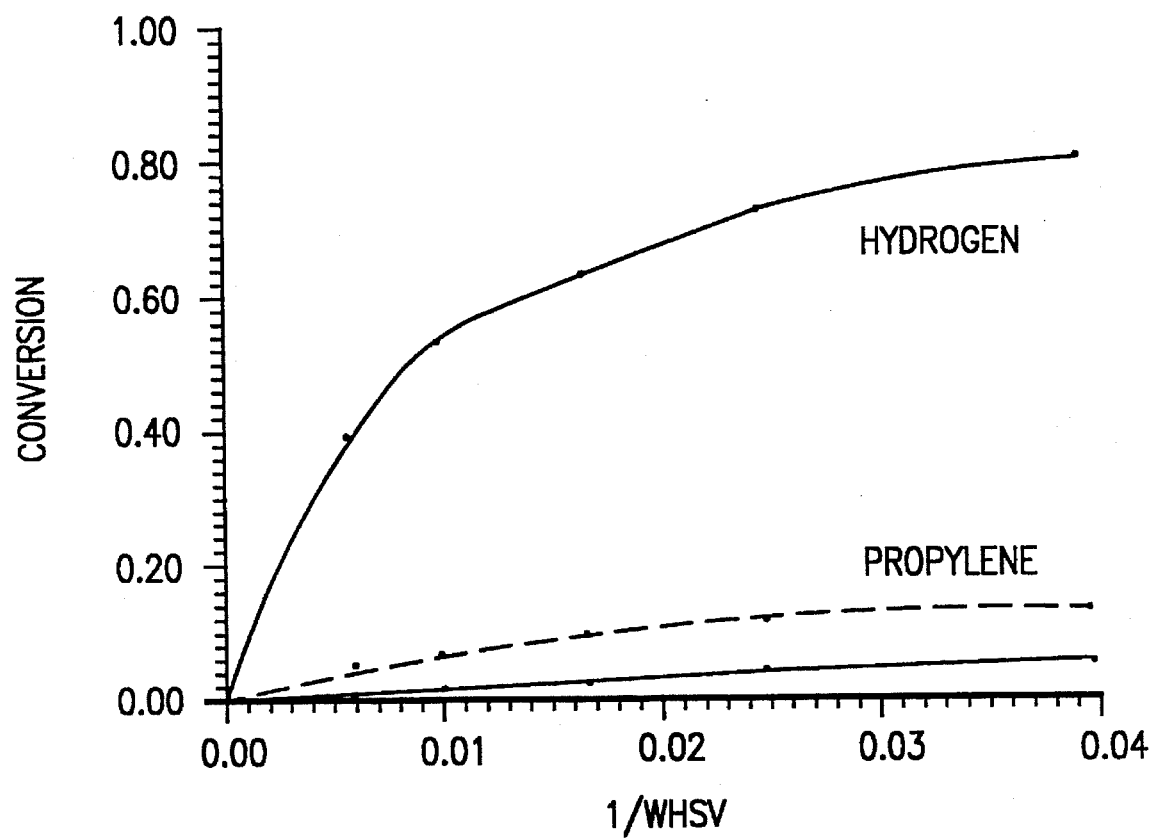
FIG. 3 is a graph showing conversions of hydrogen and propylene as a function of residence time in a reactor.

Shown in FIG. 3 are the corresponding results with a hydrogen/propylene mixture at 450° C. The solid lines correspond to a 15% $C_3$=, 15% $H_2$, 7.5% $O_2$ feed. The dashed line is the propylene conversion obtained with a 15% $C_3$, 0% $H_2$, 7.5% $O_2$ feed. The selectivity of $Bi_2O_3$ for hydrogen combustion in the presence of propylene is still high, although not as high as in the presence of propane. Furthermore, the propylene conversion is less when hydrogen is present.

EXAMPLE 8

A series of metal oxides were examined with the experiment described in Examples 2 and 3 to evaluate their SHC properties. These results of these experiments are summarized in the following table.

| Metal Oxide | Flowrate, cc/min | $H_2$Conv, % | $C_3$ = Conv., % |
|---|---|---|---|
| Silica | 170 | 10 | <0.5 |
| | 40 | <10 | 1.5 |
| $Sb_2O_3/SiO_2$ | 170 | 40 | <0.5 |
| | 40 | 16 | 1.5 |
| $Bi_2O_3/SiO_2$ | 170 | >90 | <0.5 |
| | 40 | 80 | 1.2 |
| $Bi_9PW_{12}O_x$ | 170 | 55 | 1.5 |
| | 40 | 61 | 5.5 |
| $TbO_x/SiO_2$ | 170 | 16 | 1.0 |
| | 40 | 23 | 4.0 |
| $PbO_x/SiO_2$ | 170 | 16 | <0.5 |
| | 40 | <10 | 2.5 |
| $WO_3/SiO_2$ | 170 | 22 | <0.5 |
| | 40 | <10 | 3.8 |
| $ZnO_2/SiO_2$ | 170 | 20 | 0.8 |
| | 40 | 40 | 1.5 |
| $GdO_x/SoO_2$ | 170 | 10 | <0.5 |
| | 40 | <10 | 1.5 |

-continued

| Metal Oxide | Flowrate, cc/min | $H_2$Conv, % | $C_3$ = Conv., % |
|---|---|---|---|
| $InO_x/SiO_2$ | 170 | 18 | 1.4 |
|  | 40 | 25 | 2.5 |
| $GaO_x/SiP_2$ | 170 | <10 | 6.0 |
|  | 40 | <10 | 8.4 |
| $GeO_x/SiO_2$ | 170 | <10 | <0.5 |
|  | 40 | <10 | <1.0 |

EXAMPLE 9

In this Example, it is illustrated that higher than equilibrium propylene yields from propane can be obtained by using physical mixtures of appropriate dehydrogenation catalysts with SHC metal oxides.

A physical mixture with equal weights of Pt-Sn-ZSM-5 (0.65 % Pt) and 42% $Bi_2O_3$/58% $SiO_2$ was prepared by combining pelleted, 20-40 mesh size particles of the two materials. This mixture was compared to Pt-Sn-ZSM-5 for the dehydrogenation of propane to propylene at 540° C. and 1 atm total pressure. A gas stream of pure propane was passed over 2 g of the mixed catalyst system at a flowrate of 17 cc/min for 166 sec. The reactor effluent was collected in an evacuated gas bulb and was analyzed. The same experiment was also conducted with 1 g Pt-Sn-ZSM-5. The product analysis in each case was as follows, wherein $C_3$ stands for propane, $C_3^=$ stands for propylene, $CO_x$ stands for $CO + CO_2$ and $C_3^-$ stands for cracked products.

| Catalyst | $C_3$Conv. | $C_3$ = Yield | $CO_x$Yield | $C_3$-Yield |
|---|---|---|---|---|
| Pt-Sn-ZSM-5 | 24.2 | 22.1 | 0.6 | 1.5 |
| Mixture | 47.0 | 42.0 | 3.0 | 2.0 |

EXAMPLE 10

The same experiment as in Example 9 was conducted over the mixed catalyst system, except that feed was passed over the catalyst for 332 sec. Propane conversion was 42.8%; and propylene, $CO_x$, and cracked product yields were 38.8, 1.9, and 2.0%, respectively.

EXAMPLE 11

The same experiment as in Example 9 was conducted over the mixed catalyst system, except that feed was passed over the catalyst at a flowrate of 8.5 cc/min for 332 sec. Propane conversion was 47.8%; and propylene, $CO_x$, and cracked product yields were 39.7, 4.7, and 3.4%, respectively.

EXAMPLE 12

The same experiment as in Example 9 was conducted over a mixture of 2 g Pt-Sn-ZSM-5 and 1 g $Bi_2O_3/SiO_2$. Propane conversion in the collected product was 50.2%; and propylene, $CO_x$, and cracked product yields were 40.7, 4.6, and 4.9%, respectively.

EXAMPLE 13

1 g of Pt/Sn/ZSM-5 was mixed with 1 g of the metal oxide to be tested. The catalyst mixture was first calcined in air at 550° C. and the feed was 100% propane. The feed was passed over the catalyst mixture at 17 cc/min (corresponding to WHSV=2g/gPt/Sn/ZSM5,hour) for 332 seconds. The reactor effluent was collected in an evacuated glass bulb and was analyzed. The propylene and COx yields obtained with each metal oxide are shown in Table 2 below. The base case experiment is with no metal oxide.

In Table 2, $C_3^=$sel. stands for $C_3^=$Yld divided by $C_3$ Conv.

| Catalyst | $C_3$ = yld | COxYld | $C_3$ Conv. | $C_3$ = sel |
|---|---|---|---|---|
| $Bi_2O_3/SiO_2$ | .308 | .017 | .325 | .948 |
| $BiLaOx/SiO_2$ | .301 | .022 | .323 | .932 |
| $BiSbOx/SiO_2$ | .260 | .010 | .270 | .963 |
| $Bi_2Mo_3O_{12}/SiO_2$ | .207 | .074 | .281 | .737 |
| $In_2Mo_3O_{12}/SiO_2$ | .334 | .020 | .354 | .944 |
| $In_2MoO_6/SiO_2$ | .237 | .009 | .246 | .963 |
| No Met. Oxide | .183 | .020 | .203 | .901 |
| $Al_2Mo_3O_{12}/SiO_2$ | .179 | .039 | .218 | .821 |
| $Cr_2Mo_3O_{12}/SiO_2$ | .181 | .046 | .227 | .797 |
| $MoO_3/SiO_2$ | .160 | .038 | .198 | .808 |
| $Fe_2O_3/SiO_2$ | .188 | .051 | .239 | .787 |
| $Nb_2O_3/SiO_2$ | .188 | .031 | .219 | .858 |
| $V_2O_5/SiO_2$ | .164 | .147 | .311 | .527 |

What is claimed is:

1. A process for converting an alkane of the formula, $$C_nH_{2n+2},$$

to an alkene of the formula, $$C_nH_{2n},$$

where n is the same for said alkane and said alkene and n is from 2 to 5, said process comprising contacting said alkane in the absence of cofed oxygen with a dehydrogenation catalyst and a solid oxygen source comprising a reducible metal oxide under conditions sufficient to selectively convert said alkane and reducible metal oxide to a reduced form of the metal oxide, said alkene, and water, wherein said dehydrogenation catalyst comprises Pt or Pd, and wherein said reducible metal oxide is an oxide of at least one metal selected from the group consisting of Bi, In, Sb, Zn, Tl, Pb, and Te.

2. A process according to claim 1 further comprising the steps of:
   (a) interrupting the flow of alkane into the reaction zone;
   (b) reacting the reduced form of the metal oxide with a source of oxygen under conditions sufficient to regenerate the original oxidized form of the reducible metal oxide; and
   (c) resuming the reaction in the reaction zone using the regenerated form of the reducible metal oxide.

3. A process according to claim 2, wherein steps (a), (b), and (c) are conducted periodically.

4. A process according to claim 1, wherein said alkane is ethane.

5. A process according to claim 1, wherein said alkane is propane.

6. A process according to claim 1, wherein said alkane is isobutane and/or n-butane.

7. A process according to claim 1, wherein said dehydrogenation catalyst comprises platinum.

8. A process according to claim 1, wherein said reducible metal oxide comprises an oxide of indium.

9. A process according to claim 1, wherein said reducible metal oxide comprises $Bi_2O_3$.

10. A process according to claim 1, wherein said reducible metal oxide comprises a mixed metal oxide containing bismuth.

11. A process according to claim 1, wherein said reducible metal oxide comprises $Sb_2O_4$ or a mixed metal oxide containing antimony.

12. A process according to claim 1, wherein said reducible metal oxide comprises $Bi_aSb_bO_x$, where a and b are each greater than 0 and less than or equal to 12 and x is determined by the oxidation states of Bi and Sb under reaction conditions.

13. A process according to claim 5, wherein the dehydrogenation catalyst comprises platinum, and the reducible metal oxide contains bismuth, antimony, indium, or a mixture thereof.

14. A process according to claim 1, wherein said solid oxygen source comprises a support selected from the group consisting of silica, alumina, zirconia, titania, hafnia and mixtures thereof.

15. A process according to claim 1, wherein said solid oxygen source comprises one or more oxides of an element selected from the group consisting of Mo, W, P and La.

16. A process according to claim 1, wherein said dehydrogenation catalyst and said solid oxygen source are discrete materials which do not share the same support.

17. A process according to claim 16, wherein said dehydrogenation catalyst comprises 0.1 to 20 weight percent platinum and 0.1 to 20 weight percent tin with the remainder of said dehydrogenation catalyst being ZSM-5.

* * * * *